US010195431B2

(12) United States Patent
Mesa

(10) Patent No.: US 10,195,431 B2
(45) Date of Patent: Feb. 5, 2019

(54) METHOD OF PROVIDING ELECTRICAL STIMULATION

(71) Applicant: Gabriel Mesa, Canton, CT (US)

(72) Inventor: Gabriel Mesa, Canton, CT (US)

(*) Notice: Subject to any disclaimer, the term of this patent is extended or adjusted under 35 U.S.C. 154(b) by 0 days.

(21) Appl. No.: 15/724,557

(22) Filed: Oct. 4, 2017

(65) Prior Publication Data
US 2018/0021578 A1 Jan. 25, 2018

Related U.S. Application Data

(62) Division of application No. 15/355,841, filed on Nov. 18, 2016, now Pat. No. 9,814,878.

(60) Provisional application No. 62/258,026, filed on Nov. 20, 2015.

(51) Int. Cl.
A61N 1/36 (2006.01)
A61B 5/103 (2006.01)
A61N 1/04 (2006.01)
H02N 2/18 (2006.01)
A43B 3/00 (2006.01)
H01L 41/29 (2013.01)

(52) U.S. Cl.
CPC ........ A61N 1/36021 (2013.01); A43B 3/0015 (2013.01); A61B 5/1036 (2013.01); A61N 1/0456 (2013.01); A61N 1/0492 (2013.01); A61N 1/3603 (2017.08); H01L 41/29 (2013.01); H02N 2/18 (2013.01)

(58) Field of Classification Search
None
See application file for complete search history.

(56) References Cited

U.S. PATENT DOCUMENTS

| | | | |
|---|---|---|---|
| 3,941,137 A | 3/1976 | Vredenbregt | |
| 4,926,959 A | 5/1990 | Bassett | |
| 5,052,391 A | 10/1991 | Sliberstone | |
| 7,424,325 B2 | 9/2008 | Koller | |
| 8,308,665 B2 | 11/2012 | Harry | |
| 8,569,935 B1 | 10/2013 | Kosierkiewicz | |
| 2006/0085047 A1 | 4/2006 | Unsworth | |
| 2006/0235465 A1 | 10/2006 | Koo | |
| 2007/0203533 A1* | 8/2007 | Goren | A61N 1/32 607/49 |
| 2008/0249587 A1 | 10/2008 | Cho | |

(Continued)

OTHER PUBLICATIONS

Shenck & Paradiso, Energy Scavenging with Shoe-Mounted Piezoelectrics, IEEE Micro Journal, May/Jun. 2001, pp. 30-42, vol. 21, IEEE Computern Society, United States.

(Continued)

Primary Examiner — Ankit D Tejani
(74) Attorney, Agent, or Firm — UConn IPLaw Clinic; Anthony Analo

(57) ABSTRACT

A method of providing electrical stimulation to the sole of a patient's foot is disclosed. An assembly is disclosed that comprises a non-conductive mat having an aperture and a piezoelectric device positioned to fill at least a portion of the aperture. A flexible conductive material is positioned to be in electrical contact with a first and a second primary surface of the piezoelectric device, and with the surface of the skin, providing an electric current to the skin when the piezoelectric is mechanically compressed.

3 Claims, 6 Drawing Sheets

(56) References Cited

U.S. PATENT DOCUMENTS

2010/0324455 A1\* 12/2010 Rangel ................... A43B 7/147
600/592
2014/0094873 A1 4/2014 Emborg
2014/0180376 A1 6/2014 Jennings

OTHER PUBLICATIONS

Zhao & You, A Shoe-Embedded Piezoelectric Energy Harvester for Wearable Sensors, Sensors Journal, Jul. 11, 2014, pp. 12497-12510, MDPI, Online Publication.

\* cited by examiner

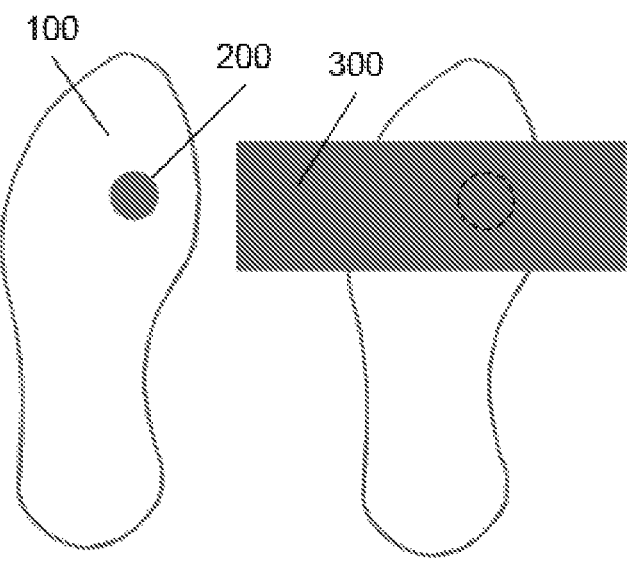
Figure 1A  Figure 1B
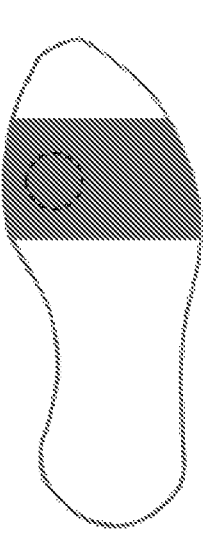
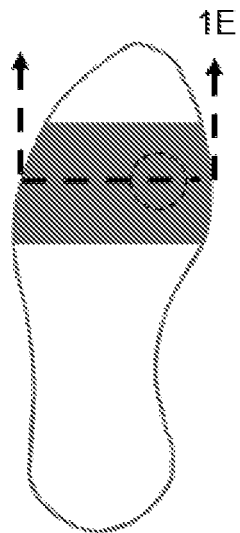
Figure 1C  Figure 1D
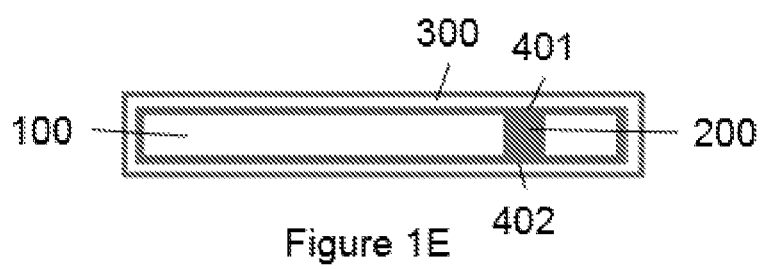
Figure 1E

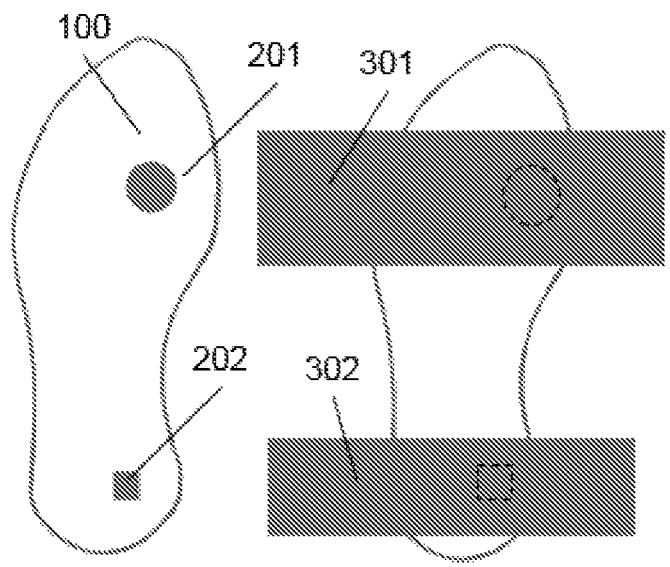
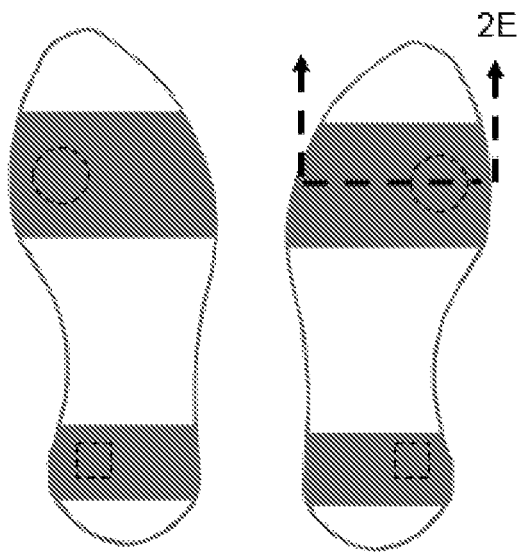
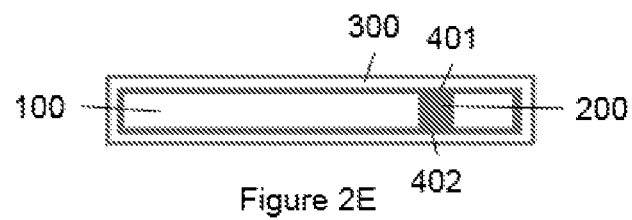

METHOD OF PROVIDING ELECTRICAL STIMULATION

CROSS-REFERENCE TO RELATED APPLICATIONS

This application is a divisional of Ser. No. 15/355,841 filed on Nov. 18, 2016, which claims priority to U.S. Provisional Application No. 62/258,026 filed on Nov. 20, 2015, which is incorporated herein by reference in its entirety.

BACKGROUND OF THE INVENTION

Diabetes is a troubling affliction that is quite common in the United States and increasing in other parts of the world. As of 2012, 9.3% of the world population suffered from diabetes. It stems from a shortage of insulin in the pancreas and causes an affliction called neuropathy. In addition to diabetes, cancer treatments, infections, and autoimmune disorders can cause neuropathy as well.

According to the Neuropathy Association, one in fifteen Americans have neuropathy, and one third of those with neuropathy have diabetic neuropathy, which is most commonly found in the foot. Over half of all amputations every year are due to diabetic neuropathy, according to the National Institute of Health. Even when the outcome of neuropathy isn't as drastic as amputation, its effects can be debilitating. Neuropathy can cause numbness, pain and weakness in the area, and it is estimated that an average annual cost of USD $1,004 is spent for pain relief medication per patient with peripheral diabetic neuropathy alone.

Traditionally, common treatments for the symptoms of neuropathy include medications, acupuncture, and physical therapy. Recently, electrical stimulation has made breakthroughs in the treatment of patients, and is a promising solution. For example, Transcutaneous Electrical Nerve Stimulation (TENS) devices may comprise two electrodes attached to patient skin, usually on the area of pain or at a pressure point, creating a circuit of electrical impulses that travel along nerve fibers. The current may alleviate the neuropathic pain of the patient. This may be because the electricity from the electrodes stimulates the nerves in an affected area and sends signals to the brain that block or "scramble" normal pain signals. Another theory is that the electrical stimulation of the nerves may help the body to produce natural painkillers called endorphins, which may block the perception of pain.

There is a need for new TENS devices which are self-powered, durable, of low cost, customizable to personal needs of each patient and can be used without affecting patients' mobility.

SUMMARY OF THE INVENTION

In one aspect the present invention provides a self-sustaining assembly for providing electrical stimulation to nerves near the surface of the skin of a patient, comprising at least one non-conductive mat, said non-conductive mat comprising a heel position and a ball position and at least one aperture located at said heel position or said ball position, and at least one piezoelectric device positioned to fill at least a portion of said aperture. The piezoelectric device has at least a first primary surface and a second primary surface generally opposed to each other and having opposing electrical charges when mechanical force is applied to the piezoelectric device. The assembly further comprises a flexible conductive material positioned to provide electrical contact between said piezoelectric device and the nerves near the surface of the skin of a patient during use. As used herein, "electrical contact" means a direct or an indirect connection that provides a path for the flow of electrical current.

In one embodiment, said flexible conductive material comprises a first conductive fabric section in electrical contact with the first primary surface of the piezoelectric device, and a second conductive fabric section in electrical contact with said second primary surface of said piezoelectric device, where said first and second fabrics are separate by a gap that is at least partially filled by skin of a patient to create a closed electrical circuit during use.

In another embodiment, said piezoelectric device is recessed within the aperture and electrical contact between the first conductive fabric section and the first primary surface is provided by an electrical lead extending between the first primary surface and the first conductive fabric section.

In another aspect, the present invention provides a method of preparing a self-sustaining assembly for providing electrical stimulation to nerves near the surface of the skin of a patient. The method comprises providing at least one non-conductive mat with an aperture as a holder for at least one piezoelectric device where the device has a first primary surface and a second primary surface, positioning the piezoelectric device in the aperture, providing a first flexible conductive fabric in electrical contact with the first primary surface and a second flexible conductive fabric in electrical contact with the second primary surface, and providing a gap between the first and second flexible conductive fabrics positioned to enable the skin of a patient to fill at least a portion of the gap and create a closed electrical circuit upon use.

In another aspect of preparing the self-sustaining device, the method further comprises recessing the piezoelectric device within the aperture and providing an electrical lead between the first flexible conductive fabric and the first primary surface of the piezoelectric device to create an electrical contact between them.

In another aspect, the present invention provides a method of providing electrical stimulation to the sole of a foot of a patient with neuropathy, comprising: (1) obtaining a prescription for a therapeutic voltage for a patient; (2) assessing the strike pattern of said patient and determining at least one location on the sole of said patient generating force in response to said strike pattern; (3) determining the amount of said force generated by said patient at said location; (4) selecting the piezoelectric device that provides said therapeutic voltage when said force is generated at said location by adjusting the thickness of said piezoelectric device, the surface area of said piezoelectric device, and the voltage constant of said piezoelectric device until said therapeutic voltage divided by said force is equal to said voltage constant multiplied by the thickness of said piezoelectric device divided by said surface area; (5) providing at least one non-conductive mat having an aperture as a holder for the piezoelectric device, said device having a first primary surface and a second primary surface; (6) positioning said piezoelectric device so as to fill at least a portion of said aperture; and (7) providing a first flexible conductive fabric in electrical contact with the first primary surface, a second flexible conductive fabric in electrical contact with the second primary surface, and a gap positioned between said first and second flexible conductive fabrics; and (8) positioning the sole of the foot so that skin fills at least a portion of the gap and so that the predetermined force is generated on the device.

Additional features and advantages are realized through the techniques of the present invention. Other embodiments and aspects of the invention are described in detail herein and are considered a part of the claimed invention.

BRIEF DESCRIPTION OF THE DRAWINGS

The subject matter which is regarded as the invention is particularly pointed out and distinctly claimed in the concluding portion of the specification. The invention, however, both as to organization and method of practice, together with the further objects and advantages thereof, may best be understood by reference to the following description taken in connection with the accompanying drawings in which:

FIG. 1A depicts an incomplete portion of the top of a shoe insole according to an embodiment of the assembly disclosed herein.

FIG. 1B depicts a further portion of the shoe insole of FIG. 1A with conductive material.

FIG. 1C depicts the completed bottom of a shoe insole of FIG. 1B with conductive material wrapped around the insole.

FIG. 1D depicts the completed top of the shoe insole of FIG. 1C.

FIG. 1E depicts a cross section as indicated in FIG. 1D.

FIG. 2A depicts an incomplete portion of the top of a shoe insole according to another embodiment of the assembly disclosed herein.

FIG. 2B depicts a further portion of the shoe insole of FIG. 2A with conductive material.

FIG. 2C depicts the completed bottom of a shoe insole of FIG. 2B with conductive material wrapped around the insole.

FIG. 2D depicts the completed top of the shoe insole of FIG. 2C.

FIG. 2E depicts a cross section as indicated in FIG. 2D.

DETAILED DESCRIPTION

Figures 3A, 3B:
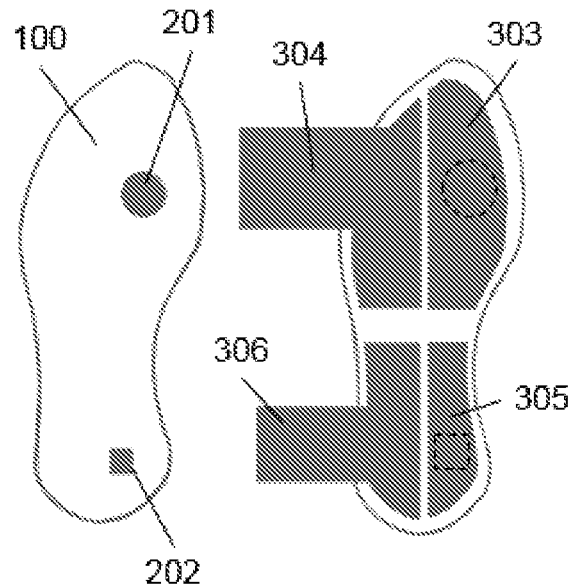
FIG. 3A depicts an incomplete portion of the top of a shoe insole according to another embodiment of the assembly disclosed herein.
FIG. 3B depicts a further portion of the shoe insole of FIG. 3A with conductive material.
Figures 3C, 3D:
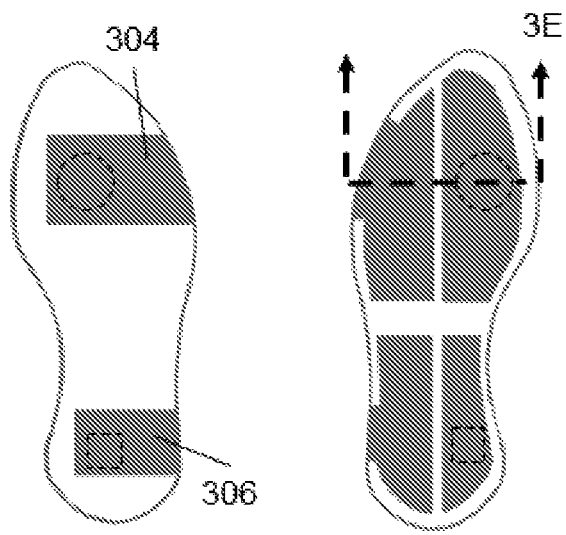
FIG. 3C depicts the completed bottom of a shoe insole of FIG. 2B with conductive material wrapped around the insole.
FIG. 3D depicts the completed top of the shoe insole of FIG. 3C.
Figure 3E:
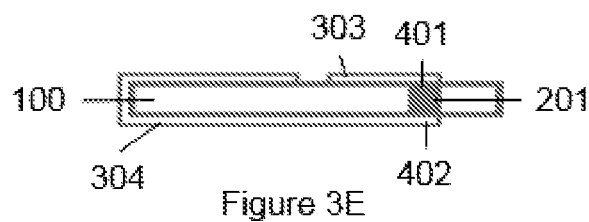
FIG. 3E depicts a cross section as indicated in FIG. 3D.
Figures 4A, 4B:
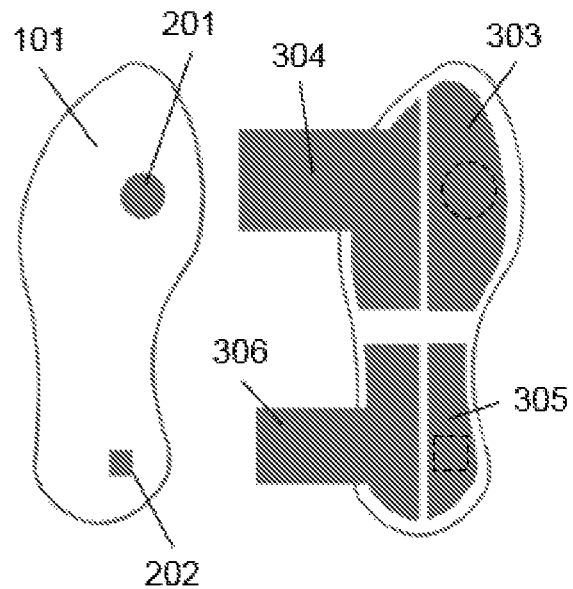
FIG. 4A depicts an incomplete portion of the top of a shoe insole according to another embodiment of the assembly disclosed herein.
FIG. 4B depicts a further portion of the shoe insole of FIG. 4A with conductive material.
Figures 4C, 4D:
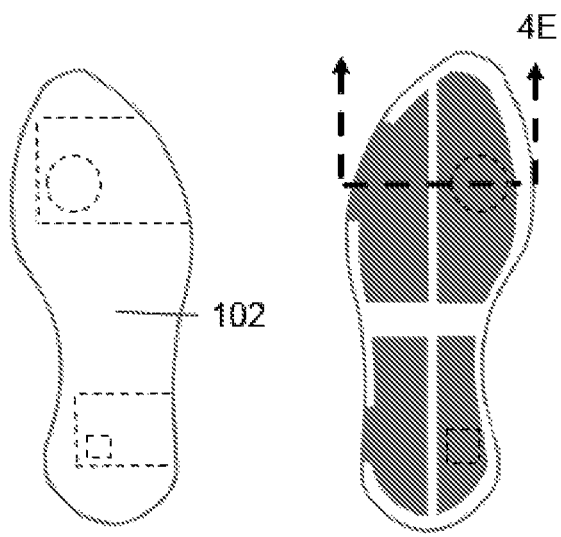
FIG. 4C depicts the completed bottom of a shoe insole of FIG. 4B with conductive material wrapped around the insole.
FIG. 4D depicts the completed top of the shoe insole of FIG. 4C.
Figure 4E:
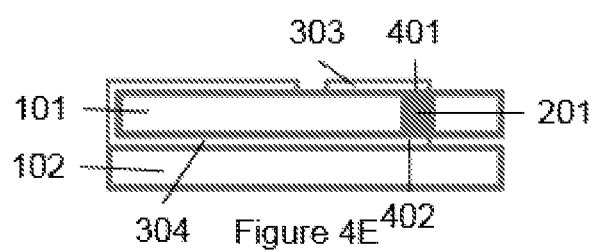
FIG. 4E depicts a cross section as indicated in FIG. 4D.
Figures 5A, 5B:
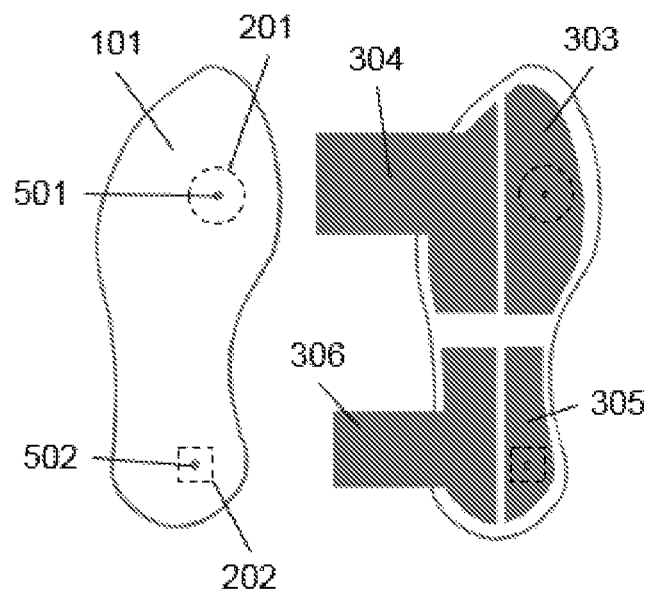
FIG. 5A depicts an incomplete portion of the top of a shoe insole according to another embodiment of the assembly disclosed herein.
FIG. 5B depicts a further portion of the shoe insole of FIG. 5A with conductive material.
Figures 5C, 5D:
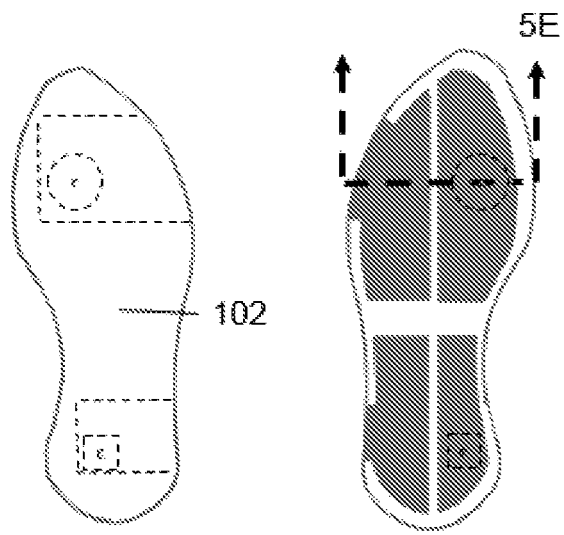
FIG. 5C depicts the completed bottom of a shoe insole of FIG. 5B with conductive material wrapped around the first layer of the nonconductive mat.
FIG. 5D depicts the completed top of the shoe insole of FIG. 5C.
Figure 5E:
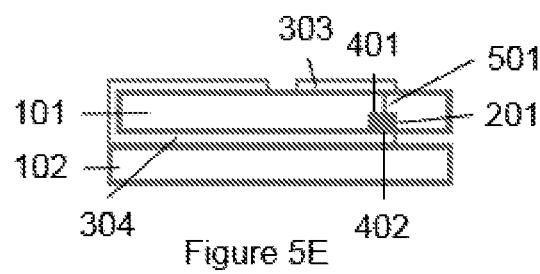
FIG. 5E depicts a cross section as indicated in FIG. 5D.

The present disclosure describes a self-sustaining assembly powered by a piezoelectric device that can, for example, alleviate pain and initiate healing in various parts of the human body, including but not limited to, the foot of a patient suffering from a type of neuropathy, e.g. diabetic neuropathy. While using the term "patient" to represent the user of the assembly described herein, any human who may benefit from such electrical stimulations to provide therapy, rehabilitation, health-promotion, or for recreational use is also intended to be included in the term "patient."

The assembly disclosed herein may be attached to or applied to various human body parts to deliver electrical current for therapeutic or other purposes. In an embodiment, the assembly is used in connection with the sole of the human foot. For example, the assembly may be incorporated into the sole of a shoe or, in the alternative, be a shoe insert, allowing for transfer between footwear of the patient. The piezoelectric device is compressed by the patient while walking, creating an electrical field, characterized by a separation of charge on primary surfaces. The primary surfaces extend generally normal to the direction of compressive force. When a conductor comes in contact with the opposing primary surfaces, the electrical circuit is completed and current flows according to the placement of the conductor. When a conductor comes in contact with a first primary surface and a separate conductor comes in contact with the second primary surface, wherein the first and second conductor are not in contact with each other because they are, for example, separated by a gap, a third conductor (e.g. the skin of the patient) is required to fill at least a portion of the gap in order to complete the circuit upon compression of the piezoelectric device.

As shown in FIG. 1A through 1E, an assembly in various stages of manufacture according to an embodiment is depicted. In FIG. 1A, a portion of the top of a shoe insole according to an embodiment of the self-sustaining assembly is depicted. FIG. 1A illustrates the top view after at least one aperture, which can be either a blind hole or a through hole, is created and sized to accommodate at least one piezoelectric device 200. The aperture is created within a non-conductive mat 100. In this embodiment, the mat 100 is shaped consistent with the right foot of a patient, however it will be appreciated that other shapes can be utilized for the nonconductive mat without departing from the scope of the claimed assembly.

FIG. 1B illustrates the top view at mid-assembly of this embodiment wherein a flexible conductive material 300 is adhered to the non-conductive mat 100, positioned in electrical contact with the first primary surface 401 (see FIG. 1E) of the piezoelectric device 200, and extended past the edges of the non-conductive mat 100. FIG. 1C illustrates the bottom view of this embodiment, wherein the extended flexible conductive material 300 has been wrapped past the sides to the bottom of the non-conductive mat 100, adhered to the bottom of the non-conductive mat 100, and positioned in electrical contact with the second primary surface 402 of the piezoelectric device 200 (see FIG. 1E). FIG. 1D illustrates a top view of this completed embodiment wherein the flexible conductive material 300 traverses a portion of both top and bottom of the non-conductive mat 100 and is positioned in electrical contact with both the first primary surface 401 and second primary surface 402 of the piezoelectric device 200. As further shown in FIG. 1E, when the piezoelectric device 200 is compressed, a completed circuit will enable current to flow according to the design, shape and position of the conductive material 300.

The non-conductive mat of the claimed assembly herein can be comprised of Silicone rubber, Spenco, PPT, Plastazote, Nickelplast, Pelite, or any other non-conductive material known in the art. The non-conductive mat functions (1) to provide the patient with comfort during walking, running, and standing; (2) to provide a support structure for the flexible conductive material between the first and second primary surfaces of a piezoelectric device; and (3) to hold the piezoelectric device in place. The material selection for the nonconductive mat is a design choice which is made based on cost, flexibility, comfort, and effects on the force delivered to the piezoelectric device by the patient during use. In one embodiment, a suitable nonconductive mat is fashioned from a rubber sheet available from Rubbercal (hhtp://www.rubbercal.com/sheet-rubber/silicone-rubber/silicone-premium-grade-red-60a.html).

As shown in FIG. 1A-E, an aperture is created in the non-conductive mat 100 in order to position the piezoelectric device 200. This aperture can be undersized compared to the size of the piezoelectric device 200 in order to hold the piezoelectric device 200 in place by compressive forces on the outside of the piezoelectric device 200. Another potential means of holding the piezoelectric device 200 in place, within an aperture that is equal or greater in size than the piezoelectric device 200, would be a non-conductive adhesive, such as loctite, epoxy, etc.

Piezoelectricity is the characteristic of certain materials to translate mechanical energy into electrical energy and vice versa. This process is due to the crystalline form of materials such as quartz, lead zirconate titanate, and Rochelle salt. Because of their unique ability to transfer between mechanical and electrical energy, they have been used in applications such as sonar detectors and scanning tunneling microscopes.

Piezoelectric devices emit an electrical charge when compressed. This is because they have a balanced internal charge. When compressed, the stress in a piezoelectric device results in a charge separation across the device producing an electric field and consequently a voltage drop. Completion of the electric circuit using a conductor allows the electric current to flow to target areas of the human body. Since piezoelectric devices do not require fossil fuels or toxic chemicals to generate electricity, they are a green energy source.

The number, shape, characteristics and location of the piezoelectric device in the self-sustaining assembly of the within invention will depend on several factors, including the location of desired treatment, location of desired force on the piezoelectric device, and the desired therapeutic frequency and voltage. More than one piezoelectric device may be utilized, for example at the ball location and the heel location of the provided nonconductive mat. For example, as shown in FIGS. 2 through 5, a ball location piezoelectric device and a heel location second piezoelectric device are utilized. In one embodiment, said ball location piezoelectric device is circular product 840 from American Piezo (https://www.americanpiezo.com/), having a diameter of 19 millimeters and a thickness of 2 millimeters, while said heel location piezoelectric device is square product 840 from American Piezo that is 10×10 (length by width) by 1.5 millimeters in thickness. The piezoelectric device may be comprised of any one of or combinations of piezoelectric material known in the art, such as ceramics, crystals, nickel, copper, or other combinations thereof.

Preferably, the piezoelectric device is placed in areas of the self-sustaining assembly which would receive the greatest, and most consistent, force during use as a result of the foot strike of the patient. This would provide the patient with a consistent therapeutic voltage during use, and can be determined from a device that measures the pressure contour of the typical foot strike of a patient. These pressure sensing devices are often floor based or in-shoe and can use piezoelectric sensor arrays or light refraction to provide a pedobarography image similar to the one shown in FIG. 7.

The process of determining the appropriate piezoelectric device for a particular patient also requires selecting the appropriate piezoelectric material for the piezoelectric device as well as the shape of the piezoelectric device. The formula for selecting an appropriate piezoelectric device for the self-sustaining assembly of the present invention is developed to account for the force generated from a typical foot strike of a patient and therapeutic voltage inputs as disclosed below:

$$(\text{Desired Voltage})/\text{Force} = (\text{Piezoelectrice Voltage Constant} \times \text{Piezoelectric Plate Thickness})/(\text{Surface Area of a First Primary Surface of a Piezoeleric Device})$$

In the above formulation, the therapeutic treatment voltage (V) should be consistent with the patient prescription or therapy requirement. The Force (expressed in Newtons) is provided from the analysis of the patient foot strike data depicted in FIG. 7 from the pressure sensing device. The remaining inputs (piezoelectric device thickness, piezoelectric voltage constant and surface area of the piezoelectric device) represent variable values based on different types or shapes of piezoelectric devices. By adjusting such variable values, the ideal piezoelectric surface area, material, and height or thickness can be determined to meet patients' personal needs and to provide the prescribed therapeutic voltage for the particular patient.

For example, if a patient who has been prescribed 18 V of low frequency treatment, and who generates 100 N of force under the ball of the foot and wants to select a piezoelectric device then the following calculations can determine the ratio of piezoelectric device thickness to piezoelectric plate surface area multiplied by piezoelectric voltage constant:

$$(18\text{ V})/(100\text{ N}) = ((\text{Piezoelectric Voltage Constant} \times \text{Piezoelectric Device Thickness})/(\text{Surface Area of a First Primary Surface of the Piezoelectric Device})(\text{V/N}))$$

Thus, the combination of piezoelectric material, thickness, and surface area of the first primary surface of a piezoelectric device can be varied until they are equal to a given a ratio of desired voltage to force generated for a given patient.

The flexible conductive material of the assembly described herein can be selected from a variety of materials that will provide suitable flow of current created by the piezoelectric device. Silver mesh fabric for example is suitable for the assembly described herein, as are other metallic materials that can be easily incorporated. In one embodiment, said flexible conductive material is silver conductive fabric from ArgenMesh (http://www.filteremf.com/buy/argenmesh/). It will further be appreciated that the shape and positioning of the conductive material of the device of the within invention will depend on the location and surface area of desired treatment. The conductive material of the device of the within invention is only required to be in electrical communication with first primary surface and second primary surface of a piezoelectric device to complete an electric circuit upon use. In one embodiment, the electrical current that is generated from the piezoelectric device travels through the flexible conductive material and provides stimulation to the patient's nerves near the surface of the sole of a foot of said patient due to the conductivity of skin in contact with the conductive material.

It will be appreciated that the flexible conductive material covering at least a portion of the non-conductive mat need not be co-extensive with the general contour of the sole of the foot, and can assume a wide range of shapes according to the desired location and area of stimulation treatment. Areas of treatment can also include other locations on the human body, including but not limited to hands, feet, arms and legs, while the electric stimulation is produced by the assembly of the present invention positioned adjacent to hands or foot soles.

As shown in FIG. 2A through 2E, an assembly in various stages of manufacture according to another embodiment is depicted. In FIG. 2A, a portion of the top of a shoe insole according to this embodiment is depicted. As shown in FIG. 2A, the piezoelectric device 200 may further comprise a first piezoelectric device 201 positioned within an aperture in the ball position of the non-conductive mat 100, and a second piezoelectric device 202 positioned within an aperture in the heel position of the non-conductive mat 100. As shown in FIG. 2B (top) and FIG. 2C (bottom), the flexible conductive material 300 of this embodiment may further comprise a first flexible conductive fabric 301 in electrical contact with the first primary surface 401 and the second primary surface 402 of the first piezoelectric device 201. A second flexible conductive fabric 302 is in electrical contact with the first primary surface 401 and the second primary surface 402 of the second piezoelectric device 202. This configuration increases the target area and frequency of the electrical stimulation for the patient.

As shown in FIG. 3A through 3E, an assembly in various stages of manufacture according to another embodiment is depicted, comprising two piezoelectric devices 201 and 202, together with a plurality of flexible conductive fabric sections 303, 304, 305 and 306. Flexible conductive fabric section 303 is only in electrical contact with the first primary surface 401 of the first piezoelectric device 201. Flexible conductive fabric section 304 is only in electrical contact with the second primary surface 402 of the first piezoelectric device 201. There is a gap between at least a portion of fabric sections 303 and second 304 to enable the conductive skin of the patient to fill the gap during use, thereby creating a closed electrical circuit. Similarly, flexible conductive fabric section 305 is only in electrical contact with the first primary surface 401 of the second piezoelectric device 202. Flexible conductive fabric section 306 is only in electrical contact with the second primary surface 402 of the second piezoelectric device 202. There is a gap between at least a portion of fabric sections 305 and 306 to enable the conductive skin of the patient to fill the gap during use, again creating a closed electrical circuit.

It will be appreciated that any number of flexible conduct fabric sections may be utilized without departing from the scope of the within invention. Tailoring the shape and location of the sections, along with the gaps separating each section, can enable a wide variety of therapeutic treatment options.

As shown in FIG. 4A through 4E, an assembly in various stages of manufacture according to yet another embodiment is depicted, comprising two piezoelectric devices 201 and 202, together with a plurality of flexible conductive fabric sections 303, 304, 305 and 306. In this embodiment, it is demonstrated how the non-conductive mat may further comprise a first non-conductive mat 101 utilized to position the first 201 and second 202 piezoelectric devices, as well as flexible conductive fabrics sections 303, 304, 305 and 306, and a second non-conductive mat 102 adhered to the first non-conductive mat 101 on the bottom side of the first non-conductive mat to provide additional comfort to the patient.

As shown in FIG. 5A through 5E, an assembly in various stages of manufacture according to yet another embodiment is depicted, comprising two piezoelectric devices 201 and 202, together with a plurality of flexible conductive fabric sections 303, 304, 305 and 306, and a first non-conductive mat 101 and a second non-conductive mat 102. In this embodiment, the apertures manufactured to position the first and second piezoelectric devices 201 and 202 are blind holes, as opposed to through holes, enabling the first primary surface 401 for each piezo electric device to be recessed within the aperture. In this embodiment, electrical connection between the first primary surface 401 of each piezoelectric device and fabric sections 303 and 305 is provided by electrical leads 501 and 502. It will be appreciated that this configuration provides even greater comfort to the patient, since the flexibility of the self-sustaining assembly will remain consistent across the surface that contacts the foot of the patient.

The assembly of the present invention may be an insert into an existing shoe, or alternatively, may be incorporated into the actual shoe insole. The piezoelectric device(s) may be embedded in any location(s) of the insole, so long as such location(s) create sufficient pressure from the foot for the piezoelectric device to produce the desired voltage when compressed.

Traditional transcutaneous electrical nerve stimulation (TENS) devices provide pain relief by obstruction of the pain gate mechanism or stimulation of the opioid system in the patient. These TENS devices use high frequency (e.g., 90-130 Hz) electrical stimulation for quick relief of pain over a much shorter duration (e.g. 30 min-2 hrs). Due to its high frequency, the stimulation cannot be maintained in long sessions, which may exceed the pain tolerance level of a patient and cause pain itself. As the result, pain may return to the patient quickly after the TENS stimulation stops.

The alternative to high frequency TENS treatment is low frequency treatment, which has long-lasting pain relief effects due to the continuous treatment. However, traditional TENS devices are usually not portable and most importantly, the treatment to human body, e.g., the bottom of the foot, requires the patient sit and remain immobile for the whole session of treatment. Thus, extended time periods of treatment are inconvenient to the patient's everyday life.

The present disclosure provides an assembly using low frequency electrical pulses without impairing the mobility of the patient. In one embodiment, the frequency of stimulation is generated by the frequency of the patient's step. This assembly allows the patient to walk or run freely during treatment. In addition, the patient has thus an incentive to stay mobile and is rewarded for physical activity with pain relief, which contributes to long lasting nerve regenerating effects for rehabilitation.

The term "low frequency" refers to any frequency of electrical pulses/currents lower than the traditional TENS frequency and suitable for the patient's need for treatment or rehabilitation. Thus, any frequency below 90 Hz would be classified as "low frequency" treatment.

The average walking cadence for a human is about 117 steps per minute or 58.5 steps per minute per foot (nearly one step per second). In order to generate electrical charges at the required low frequency (such as from about 2 to about 5 Hz, which means 2-5 times per second) for therapy, the assembly of the present disclosure may comprise at least one piezoelectric device for releasing charges. In the case of multiple (e.g., two) piezoelectric plates, each may generate a charge during a different part of the step process of human foot during walking or running. Thus, more piezoelectric plates embedded in the shoe insole increase the frequency of electric stimulation that is to be delivered to the bottom of foot during walking, standing, or running.

Figures 6A, 6B, 6C, 6D:
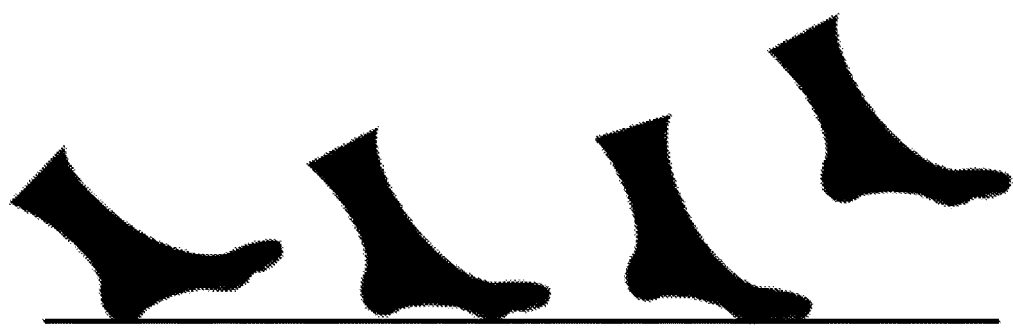
FIG. 6A depicts the heel strike phase of a typical step.
FIG. 6B depicts the support phase of a typical step.
FIG. 6C depicts the push off phase of a typical step.
FIG. 6D depicts the swing phase of a typical step.

As exemplified in FIG. 6, there are generally four phases to each step. FIG. 6A illustrates the first phase which is dorsiflexion or heel strike. FIG. 6B illustrates the second phase which is the support phase where the entire sole is on the ground. FIG. 6C illustrates the third phase which is the plantarflexion of push off from the ball of the foot. FIG. 6D illustrates the fourth and final phase which is the lift off or swing phase. During the first phase, pressure is placed on the heel and will compress a piezoelectric device placed in the heel position of an assembly as disclosed herein to deliver electric stimulation as provided above. During the second phase, pressure is placed on the heel and the ball of the foot and will compress a piezoelectric device placed in the heel position and in the ball position of an assembly as disclosed herein to provide electric stimulation as provided above. During the third phase the heel is lifted so that the electric stimulation is only produced by the ball positioned piezoelectric device. During the final phase the entire foot is lifted and no electric stimulation is delivered. Thus, low frequency electrical stimulation is achieved by the assembly described herein during walking and running by a patient.

The process of determining the appropriate piezoelectric device of the within invention for a particular patient also requires a determination of the appropriate voltage. In order to determine the exact voltage of stimulation required during low frequency treatment, a physician or others may assess the patient and make a prescription for low frequency therapy based on the patient's personalized information, such as the severity of disease/symptoms, the levels of pain tolerance, and response to previous TENS treatment, etc. The traditional prescriptions used in TENS treatment are from about 1 to about 110 Volts.

Figure 7:
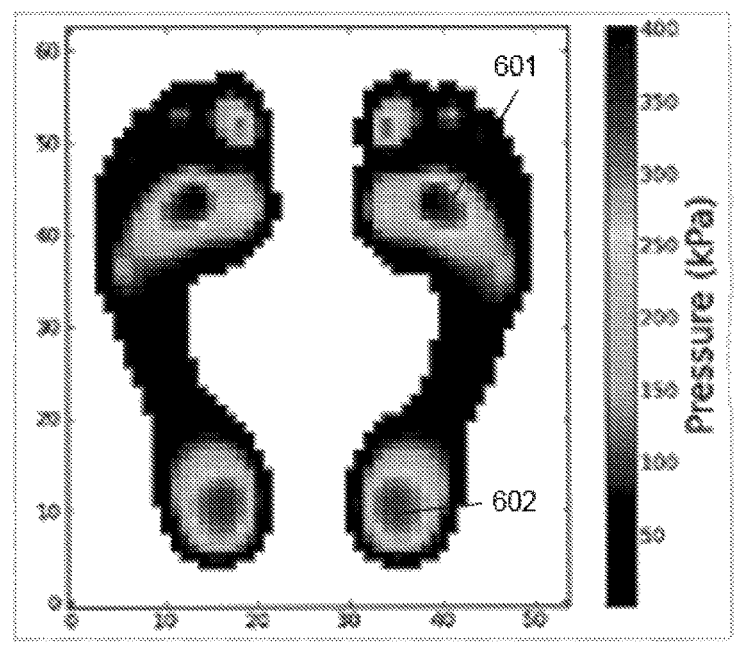
FIG. 7 depicts an exemplary image of the pressure contour on the foot of a patient.

Once a low frequency therapy is deemed appropriate and an appropriate voltage has been determined, the optimal position for a particular piezoelectric device within the self-sustaining device of the within invention can be determined. In the embodiment where the device of the within invention is directed to supplying electrical stimulation to the foot, a personal foot strike pattern can be analyzed. The science of pedobarography assesses these pressure contours and produces visual representations of a patient's strike pattern. There are many different types of devices for measuring foot pressure. A typical device in pedobarography determines the areas of the patient's sole which sustain pressure. An exemplary pedobarography image is depicted in FIG. 7, where high pressure areas 601 and 602 are identified.

It will be appreciated that multiple piezoelectric devices having different characteristics such as piezoelectric constant, thickness and contact surface area may be utilized in a single device without departing from the self-sustaining device of the within invention. By the same token, multiple types of conductive material with various shapes may be utilized in a single device without departing from the self-sustaining device of the within invention. It will further be appreciated that while the human foot has been discussed in connection with several embodiments of the within invention, other areas of the human body can also be treated with a piezoelectric device of the within invention. By way of example, a piezoelectric device can be created for the treatment of neuropathy in the hands, using the assembly described herein, where the piezoelectric device is mechanically compressed by way of squeezing the hands together to create an electric current. The force of this activity and the relevant surface area are measured by an appropriate device to provide the required inputs for determining the requisite piezoelectric component. Gloves can then be fashioned using a conductive material contacting exposed primary surfaces of the piezoelectric device to deliver electrical stimulation to the desired areas of the hands. Further, the produced electric current may be transferred to other parts of human body for the same therapeutic or rehabilitation purposes. For example, the piezoelectric materials may be embedded in a shoe insole or a glove as described herein, while the electric current produced by stepping the foot during standing, walking, or running or by squeezing the hand may be transferred through a flexible conductive material (e.g., an electric cord, etc.) to a patch attached to skin of other parts of human body. Thus, the foot or the hand works as a "generator" to produce electric stimulation delivered to any parts of body. Moreover, the piezoelectric device, wrapped in a conductive material or fabric, may be placed in the tip of a massager or a massager knock hammer, which may be used by a patient to touch or press body skin to produce electric stimulation. By this design, the patient may control the strength and/or the frequency of the produced electric stimulation.

The exemplary devices and methods in the present disclosure are illustrative of specific embodiments of the invention, and various uses thereof. They are set forth for explanatory purposes only, and should not be construed as limiting the scope of the invention in any way.

It is understood that while the invention has been described in conjunction with the detailed description thereof, the foregoing description is intended to illustrate and not limit the scope of the invention, which is defined by the scope of the appended claims. The materials, methods, and examples are illustrative only and not intended to be limiting. All publications, patent applications, patents, sequences, database entries and other references cited and described herein are incorporated by reference in their entireties. Other aspects, advantages and modifications are within the scope of the following claims.

What is claimed is:

1. A method of providing electrical stimulation to the sole of a foot of a patient with neuropathy, comprising:
   obtaining a prescription for a therapeutic voltage for a patient;
   assessing the strike pattern of said patient and determining at least one location on the sole of said patient generating force in response to said strike pattern;

determining the amount of said force generated by said patient at said location;

selecting a piezoelectric device that provides said therapeutic voltage when said force is generated at said location by adjusting the thickness of said piezoelectric device, the surface area of said piezoelectric device and the voltage constant of said piezoelectric device until said therapeutic voltage divided by said force is equal to said voltage constant multiplied by the thickness of said piezoelectric device divided by said surface area;

providing at least one non-conductive mat having an aperture as a holder for the piezoelectric device, said device having a first primary surface and a second primary surface;

positioning said piezoelectric device so as to fill at least a portion of said aperture; and providing a first flexible conductive fabric in electrical contact with the first primary surface, a second flexible conductive fabric in electrical contact with the second primary surface, and a gap positioned between said first and second flexible conductive fabrics positioning the sole of the foot on the device so that skin fills at least a portion of the gap and so that the predetermined force is generated on the device.

2. The method of claim 1, wherein the piezoelectric device is recessed within the aperture and said electrical contact between said first conductive fabric section and said first primary surface further comprises an electrical lead extending between said first primary surface of the piezoelectric device and said first flexible conductive fabric section.

3. The method of claim 1, wherein the flexible conductive material comprises silver mesh.

* * * * *